United States Patent
Bak et al.

(12)

(10) Patent No.: US 6,403,868 B1
(45) Date of Patent: Jun. 11, 2002

(54) GUZMANIA PLANT NAMED 'TEMPO'

(75) Inventors: Elly Bak, Rijsenhout; Nicolaas D.M. Steur, 1734 JL Oude Niedorp, both of (NL)

(73) Assignee: Corn. Bak B.V., Assendelft (NL)

( * ) Notice: Subject to any disclaimer, the term of this patent is extended or adjusted under 35 U.S.C. 154(b) by 0 days.

(21) Appl. No.: 09/592,966

(22) Filed: Jun. 13, 2000

Related U.S. Application Data

(63) Continuation-in-part of application No. 09/343,211, filed on Jun. 30, 1999.

(51) Int. Cl.⁷ .................................................. A01H 5/00

(52) U.S. Cl. ....................................... 800/323; 800/260

(58) Field of Search ................................. 800/323, 300

(56) References Cited

PUBLICATIONS

Benzing, David H., "The Biology Bromeliads", Mad River Press, Eureka, CA, pp 1–287 (1980).

Rauh et al., "Bromelien Tillandsien und andere kulturwurdige Bromelien", *Eugen Ulmer, Stuttgart, Germany, pp* 7–68 (1981).

Zimmer et al., "Bromelien Botanik und Anzucht ausgewahlter Arten", Parey, Berlin; Hamburg, Germany, pp 9–94 (1986).

*Primary Examiner*—Bruce R. Campbell
*Assistant Examiner*—June Hwu
(74) *Attorney, Agent, or Firm*—Foley & Lardner

(57) ABSTRACT

A new cultivar of Guzmania plant named 'Tempo' particularly characterized by its solid, compact growth habit in a funnel-form rosette; numerous, relatively narrow leaves; superior floral bract production; star-shaped inflorescence; bright, relatively deep red floral bracts; and long-lasting habit.

5 Claims, 1 Drawing Sheet

(1 of 1 Drawing Sheet(s) Filed in Color)

US 6,403,868 B1

GUZMANIA PLANT NAMED 'TEMPO'

This is a continuation-in-part application of U.S. patent application Ser. No. 09/343,211, filed Jun. 30, 1999, now U.S. Pat. No. PP12124.

FIELD OF INVENTION

The present invention relates to a new and distinct cultivar of Guzmania that is a hybrid, hereinafter referred to by the cultivar name 'Tempo'. The present invention relates to seeds which are Guzmania cultivar 'Tempo', as well as plants and plant parts produced from these seeds which have all the morphological and physiological characteristics of the Guzmania cultivar 'Tempo'. The present invention also relates to methods for producing these seeds and plants. Furthermore, the present invention relates to a method of producing progeny Guzmania plants by crossing Guzmania cultivar 'Tempo', as the male or female parent, with another Guzmania plant and selecting progeny.

BACKGROUND OF THE INVENTION

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Typically, the plants are shaded from direct sunlight. During the spring to autumn period, the central vase-like part of the leaf rosette is normally filled with water.

Guzmania is native to tropical America. Leaves of Guzmania are usually formed as basal rosettes which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots which can be detached from the mother plant and grown in an appropriate soil or bark mixture.

Methods for cultivation and crossing of Guzmania are well known. For a detailed discussion, reference is made to the following publications, which are incorporated herein by reference: Benzing, David H., *THE BIOLOGY OF THE BROMELIADS*, Mad River Press, Inc., Eureka (1980); Zimmer, Karl, *BROMELIEN*, Verlag Paul Parey, Berlin (1986); and Rauh, Werner, *BROMELIEN*, Verlag Eugen Ulmer, Stuttgart (1981).

A Guzmania inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect to their morphological and physiological characteristics.

A need exists for a greater variety of Guzmania cultivars with attractive ornamental features. Additionally, a need exists for additional Guzmania hybrid cultivars that can be easily propagated by seed.

SUMMARY OF THE INVENTION

These and other objectives have been achieved in accordance with the present invention which provides a new cultivar 'Tempo' that is a product of a planned breeding program undertaken by the inventors in Assendelft, The Netherlands, in 1993. The male or pollen parent was a selection of *Guzmania lingulata minor* identified by Code No. 93523011. The female or seed parent was a selection of *Guzmania lingulata lingulata* identified by Code No. 93523272.

Both parents have a sufficient degree of homozygosity such that the progeny of the cross are genetically and phenotypically uniform. The cultivar 'Tempo' therefore can be produced by sexual reproduction by crossing 93523011× 93523272 to produce a population of progeny plants, each of which has the combination of characteristics as herein disclosed for the new cultivar. Seeds which are cultivar 'Tempo' are produced by crossing 93523011×93523272 and have been deposited with the American Type Culture Collection, 10801 University Boulevard, Manassas, Va. 20110-2209, and accorded Deposit Accession No. PTA-3291. 2500 seeds were deposited with the ATCC on Apr. 16, 2001.

The cultivar 'Tempo' can also be produced by asexually reproducing progeny from the cross of 93523011×93523272 because the combination of characteristics as herein disclosed for the new cultivar 'Tempo' are firmly fixed and are retained through successive generations of asexual reproduction.

OBJECTS OF THE INVENTION

This invention relates to seeds which produce Guzmania cultivar 'Tempo'.

This invention also relates to Guzmania plants, and parts thereof, having all the physiological and morphological characteristics of Guzmania cultivar 'Tempo'. This invention relates to a plant produced from seeds which are Guzmania cultivar 'Tempo'. This invention also relates to plant parts, such as pollen, seeds or inflorescence produced by Guzmania cultivar 'Tempo'.

This invention relates to a method of producing seeds which are Guzmania cultivar 'Tempo', by crossing *Guzmania lingulata lingulata* selection 93523272 as the female parent with *Guzmania lingulata minor* selection 93523011 as the male parent and the reciprocate cross with 93523272 as the male parent and 93523011 as the female parent and harvesting seeds produced from said crosses.

This invention also relates to a method of producing plants having all the physiological and morphological characteristics of the Guzmania cultivar 'Tempo' comprising the steps of (a) crossing *Guzmania lingulata lingulata* selection 93523272 as the female parent with *Guzmania lingulata minor* selection 93523011 as the male parent; (b) harvesting seeds produced from said cross; and (c) producing plants from said harvested seeds.

The invention also relates to producing progeny plants from the cross of Guzmania cultivar 'Tempo', as the male or female parent, with another Guzmania plant, and selecting progeny plants for this cross.

BRIEF DESCRIPTION OF THE FIGURES

The file of this patent contains at least one drawing executed in color. Copies of this patent with the color drawing(s) will be provided by the Patent and Trademark Office upon request and payment of the necessary fee.

The photographic drawing shows a side view of the inflorescence and foliage characteristics of 'Tempo', with colors being as true as possible with illustrations of this type.

DETAILED DESCRIPTION

This invention is directed to a Guzmania plant having all the morphological and physiological characteristics of the cultivar 'Tempo' produced from seeds which are the product of the cross of *Guzmania lingulata lingulata* selection 93523272 as the female parent with *Guzmania lingulata minor* selection 93523011 as the male parent. Both parents have a sufficient degree of homozygosity such that the progeny of the cross were, and continue to be, phenotypically uniform. The variety 'Tempo' therefore can be produced by sexual reproduction by crossing 93523272× 93523011 to produce a population of progeny plants each of which has the combination of characteristics as herein disclosed for the new cultivar.

The variety 'Tempo' can also be produced by asexually reproducing progeny from the cross of 93523272×93523011 because the combination of characteristics as herein disclosed for the new cultivar 'Tempo' are firmly fixed and are retained through successive generations of asexual reproduction. The selection comprising the new variety was chosen after commencement of flowering of the progeny in 1996 in Assendelft, The Netherlands. The selection was first asexually propagated through offshoots by, or under the supervision of, the inventors in Assendelft, The Netherlands, with subsequent asexual reproduction being primarily by offshoots. Sexual and asexual propagation has demonstrated that the combination of characteristics as herein disclosed for the new cultivar 'Tempo', as observed in Assendelft, The Netherlands, are firmly fixed and are retained through successive generations of asexual reproduction.

'Tempo' is particularly characterized by the following characteristics:

1. solid, compact growth habit in a funnel-form rosette measuring approximately 19 cm in height above the pot when flowering; the cultivar is small both in height and overall diameter;
2. numerous, relatively narrow leaves, each approximately 2–3 cm in width and 21 cm in length;
3. superior floral bract production;
4. star-shaped inflorescence;
5. floral bracts are a bright, relatively deep red, which especially distinguishes the new cultivar from others, including the cultivar 'Intro' disclosed in Plant U.S. Pat. No. 10,852; and
6. long-lasting habit.

'Tempo' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar.

For example, substantial differences in plant height and diameter, and the number of leaves, can result depending on the size of the plant at the time flowering is induced by acetylene treatment. Since treatment with acetylene to induce flowering disrupts normal watering and fertilization regimens, acetylene treatment of relatively smaller plants adversely affects the growth of the plant.

The following traits have been repeatedly observed and in combination distinguish 'Tempo' as a new and distinct cultivar. These observations, measurements and descriptions were taken for 'Tempo' plants grown under the following greenhouse conditions in Assendelft, The Netherlands. The minimum day and night temperatures were 20° and 18° C., respectively. The ventilation temperature was 24° C., and the maximum light intensity was 18000 Lux. Fertilizer concentration was 0.5 to 1 EC comprising N:P:K in the ratio of 1:0.25 to 0.5:2 to 3. In addition, 3% of the total amount of fertilizer was $MgSO_4$ (15% MgO).

Frequency of fertilization varied depending on time of year and ranged from once per week to once per month. Fertilization was more frequent during the spring and summer months. Following fertilization, the plants were rinsed with sufficient clean water to remove residual fertilizer from the leaves. If fertilization frequency, or the concentration of fertilizer, is increased, 'Tempo' leaves are darker in color, eventually resulting in burning of leaves and roots. If fertilization frequency, or the concentration of fertilizer, is decreased, 'Tempo' leaves are lighter in color. If the ratio of N:K is increased above the value given above, 'Tempo' leaves become darker in color, longer and more narrow. If the ratio of N:K is decreased below the value given above, 'Tempo' leaves become lighter in color, shorter and broader. The intensity of the color of the inflorescence depends also on the amount of P.

With regard to induction of flowering, acetylene gas is allowed to bubble through 100 L of cool water for 30 min. at a pressure of 0.5 bar. Whole plants are then sprayed with the acetylene solution, making certain that the cup (vase) is filled. Spraying is done in the morning because the plants need light after this treatment, and the plants are not watered again for at least two days. The plants are treated again, following this same protocol, one week later. The plants should not be fertilized for two to three weeks following treatment with acetylene because it is likely the flowers will not form and the bracts will remain green. The description of the new cultivar 'Tempo' reported herein is based on measurements and observations of plants grown from seeds.

The following traits have been repeatedly observed to be characteristics which, in combination, distinguish Guzmania 'Tempo' from the closest comparison cultivar, Guzmania 'Intro'. The most important difference is the color of the inflorescence. Guzmania 'Tempo' is red (RHS 44A) and Guzmania 'Intro' is gray-purple (RHS 185A).

PLANT

| | |
|---|---|
| Form: | Funnel-form rosette. |
| Height: | Approximately 19 cm high, when flowering. |
| Growth Habit: | Stemless. |
| Diameter: | Approximately 40 cm. |
| Variation: | The foregoing dimensions can vary substantially depending on the timing of the acetylene treatment to induce flowering. When the plant is treated as a relatively small plant, the height and diameter of the plant will be smaller than if acetylene treatment is carried out on a much older and larger plant. This is well-known to those skilled in the art, with size of plant being controlled by the grower based on the timing of the acetylene treatment. |

FOLIAGE

| | |
|---|---|
| Color (upper surface): | RHS 144A to RHS 146A |
| Color (under surface): | RHS 146B to RHS 146C (the color of the leaves can change depending on environmental conditions). |
| Size of Leaf: | Length is approximately 21 cm and width is approximately 2–3 cm. |

-continued

| | |
|---|---|
| Shape of leaf: | Linear-lanceolate. |
| Surface Texture: | Smooth. |
| Orientation: | Leaf blades arch continuously from base. |
| Variegation: | None. |

BRACTS

Length:

| | |
|---|---|
| Scape bracts: | The lowest scape bracts are approximately 14 cm long. The scape bracts just below the primary bracts are approximately 9 cm long. |
| Primary bracts: | The lowest primary bracts are approximately 10 cm long. The bracts progress upwardly, they become shorter, with the top primary bracts being approximately 5 cm in length. |
| Width: | The scape bracts are approximately 3–3.5 cm wide and the primary bracts are approximately 3 cm wide. |
| Number: | There are approximately 8 scape bracts and 14 primary bracts, which combine to make a full inflorescence. |
| General Shape: | Recurved and ovate-lanceolate. |
| Texture: | Smooth. |
| Margin: | Entire. |
| Color: | The primary bracts are RHS 44A and the tip of the top primary bracts is RHS 17A. |

INFLORESCENCE

| | |
|---|---|
| Borne (stalks): | Erect. |
| Shape of inflorescence: | Singular (head). |
| Size of inflorescence on stalk: | The size of the inflorescence changes with maturity; at full flowering, inflorescence is approximately 7 cm in height and approximately 13 cm in diameter. |

FLOWERS

| | |
|---|---|
| Individual petals: | (Mostly disposed within the inflorescence.) |
| Length: | Approximately 5.5 cm |
| Width: | Approximately 0.5 cm |
| Quantity: | Approximately 25 flowers depending on the size of the plant. |
| Color: | RHS 17A with a white top |
| Time of Blooming: | A fully grown plant can bloom the whole year starting approximately nine (9) weeks after natural induction or through treatment with acetylene. |
| Duration of blooms: | Each flower blooms one (1) day and the total of blooming is about six (6) weeks. |

REPRODUCTIVE ORGANS

| | |
|---|---|
| Ovaries: | Superior. |
| Stamens: | Six (6) in number. |

SEED CHARACTERISTICS

| | |
|---|---|
| Quantity: | Approximately 5000 seeds divided over approximately 20 capsules (depending on the size of the plant). |
| Texture: | The seeds are plumose. |
| Other: | This cultivar is a hybrid and, therefore, the seeds cannot be used for reproduction of 'Tempo'. |

We claim:

1. A seed having American Type Culture Collection Deposit Accession No. PTA-3291 produced by crossing a Guzmania selection identified by Code No. 93523011 with a Guzmania selection identified by Code No. 93523272, said seed producing a plant that is particularly characterized by the following:

(a) solid, compact growth habit in a funnel-form rosette measuring approximately 19 cm in height above a pot when flowering;

(b) numerous, relatively narrow leaves, each approximately 2–3 cm in width and 21 cm in length;

(c) approximately 8 scape bracts and 14 primary bracts;

(d) star-shaped inflorescence;

(e) bright, relatively deep red floral bracts which especially distinguish this new cultivar from others, including the cultivar 'Intro' disclosed in Plant Pat. No. 10,852; and (f) long-lasting habit.

2. A Guzmania plant designated cultivar 'Tempo' produced from seed accorded American Type Culture Collection Deposit Accession No. PTA-3291.

3. The pollen produced by the plant according to claim 2.

4. The inflorescence produced by the plant according to claim 2.

5. A method of producing Guzmania progeny plant comprising the steps of (a) crossing Guzmania cultivar 'Tempo' produced from seed accorded American Type Culture Collection Deposit Accession No. PTA-3291 with another Guzmania plant and (b) selecting progeny.

\* \* \* \* \*